US010596286B2

(12) United States Patent
Casares

(10) Patent No.: US 10,596,286 B2
(45) Date of Patent: Mar. 24, 2020

(54) DEVICE TO ELIMINATE GERMS AND BACTERIA FROM YOUR HANDS

(71) Applicant: Carlos Maxwell Casares, Buenos Aires (AR)

(72) Inventor: Carlos Maxwell Casares, Buenos Aires (AR)

( * ) Notice: Subject to any disclaimer, the term of this patent is extended or adjusted under 35 U.S.C. 154(b) by 126 days.

(21) Appl. No.: 15/871,204

(22) Filed: Jan. 15, 2018

(65) Prior Publication Data

US 2018/0214588 A1 Aug. 2, 2018

Related U.S. Application Data

(60) Provisional application No. 62/447,004, filed on Jan. 17, 2017.

(51) Int. Cl.
*A61L 2/20* (2006.01)
*G08B 21/24* (2006.01)

(52) U.S. Cl.
CPC ........... *A61L 2/202* (2013.01); *A61L 2202/11* (2013.01); *A61L 2202/13* (2013.01); *A61L 2202/14* (2013.01); *A61L 2202/21* (2013.01); *G08B 21/245* (2013.01)

(58) Field of Classification Search
CPC ..... A61L 2/10; A61L 2/16; A61L 2/20; A61L 2/202; A61L 2/22; A61L 2/24; A61L 2202/11; A61L 2202/12; A61L 2202/122; A61L 2202/13; A61L 2202/14; A61L 2202/15; G08B 21/245
See application file for complete search history.

(56) References Cited

U.S. PATENT DOCUMENTS

| 3,278,256 A | * | 10/1966 | Skaller | A61L 2/06 219/390 |
| 2010/0266446 A1 | * | 10/2010 | Constantacos | A61L 2/0047 422/24 |
| 2013/0224076 A1 | * | 8/2013 | Hansmann | A61L 2/0094 422/111 |
| 2018/0339072 A1 | * | 11/2018 | Foster | A61L 2/0088 |

* cited by examiner

*Primary Examiner* — Timothy C Cleveland
(74) *Attorney, Agent, or Firm* — DeFillo & Associates, Inc.; Evelyn A DeFillo

(57) ABSTRACT

The present invention relates to a device that eliminates germs and bacteria from your hands. The device is especially designed to achieve total asepsis of the hands of people working and/or should have access to certain sectors of industries manufacturing and/or fractionation of food, medicinal products, testing laboratories industry biological, chemical industries in general, operating rooms, etc. where it is required to maintain strict hygiene and asepsis conditions.

12 Claims, 4 Drawing Sheets

DEVICE TO ELIMINATE GERMS AND BACTERIA FROM YOUR HANDS

CROSS-REFERENCE TO RELATED APPLICATIONS

This application claims the benefit of priority to U.S. Provisional Application No. 62/447,004, filed Jan. 17, 2017, the contents of which are incorporated herein by reference.

FIELD OF THE INVENTION

The present invention relates to a device to achieve the asepsis of working people's hands and/or that need to access certain sectors of the manufacturing industries and/or food fractionation, medicinal products industries, biological analysis laboratories, chemical industries in general, operating rooms, etc. where it is required to maintain strict hygiene and asepsis conditions.

BACKGROUND OF THE INVENTION

As prior art in the field, there are currently known and used devices for hand washing with soap or detergent dispensers to wash the hands in order to remove fatty substances adhered to the hands, impurities and/or residues that may contain particles, germs and/or bacteria contaminants that need to be eliminated. These devices are used both for personal hygiene as well as to preserve the hygienic conditions of certain areas where all types of contamination should be avoided. After the use of soap or detergent, the hands must be rinsed with water and then dried. Some soap or detergent dispensers are located adjacent to a water faucet for rinsing, or include the water deposit as its structure, and in other cases include a hand dryer with a hot or cold air jet.

Undoubtedly, these types of hand-cleaning devices, even when they are extremely practical to wash hands when they are installed in public toilets, businesses bathrooms, and industrial plants in general, are not sufficiently appropriate for their use where you should proceed to the elimination of germs and bacteria that might be contained in the hands, for example, in facilities for manufacturing and/or fractionation of food, medicinal products industries, biological analysis laboratories, chemical industries in general, operating rooms, etc., i.e., where it is required to maintain strict hygiene and asepsis conditions.

In addition, the soap, alcohol in gel, or hydro-alcoholic lotion which are known in the market, disinfect only by contact, thus, it requires a technique for hand-washing that allows such sanitizers to come into contact with the entire surface of the hands.

This technique is only used by 30% of people who must have total asepsis of hands (including doctors).

In order to resolve the limitations of devices, such as those previously mentioned, it has developed, for example, a device which allows hand disinfection control of people allocated to specific tasks in installations in general where is required a strict maintenance of total aseptically. This device includes a biometric reader of digital scan able to recognize and record patterns of human body determined by skin features such as fingerprint and the palm of the hands of individuals. The biometric reader is attached to a dispenser of antiseptic substance in a container provided for this purpose. When it detects dirt on the hands, it doses a ration of the disinfectant in the hand of the employee under control. The biometric reader is connected to electronic signs, strategically located, for sending custom periodic notices ordering each employee in particular to proceed to the corresponding hygiene control, allows to monitor the frequency of hand washing, and by a command of power door locks in various sectors to determine in practice, enables or restricts access to places where the staff should enter only when it has strictly fulfilled the hygiene conditions. From the beginning of the working day and until its completion, the device allows to obtain a record of presence, working time of staff and hygiene monitoring schedules, detecting the entry and exit of employees at their workplace starting from the reading of the fingerprint. In addition, the device can be connected to screens located in strategic positions, as appropriate in each place of application, by means of which it periodically informs the concerned employees that he/she should proceed with their hand hygiene control, thus overseeing the development of the employee.

While this device is a major technical breakthrough with regard to the previous ones, it's most relevant characteristics are related to the identification and control of any persons who have or not proceeded to wash their hands with antiseptic substances, but does not ensure the effective elimination of germs and bacteria from the hands, as is instead achieved by the device-object of the present invention.

SUMMARY OF THE INVENTION

Considering the need to ensure efficient total disinfection of hands of those who develop their common tasks or need to access certain sectors where it is essential to preserve strict aseptic conditions, the device-object of the present invention has been developed. In effect, being the hands are normally clean, i.e. e.g. washed with soap, detergent, or medical alcohol, by means of the device which is described and claimed is possible to eliminate germs and bacteria that remain both on the palm and the back of the hands, between the fingers, and in the space between the tip of the nail and finger.

This is achieved through the generation and emission of an ozone cloud inside a cabinet where the user should place his/her hands, where the ozone is distributed completely wrapping the hands during a predetermined time to complete the disinfection, ensuring total hand asepsis. As it is known, ozone has a great penetration capacity and germicidal and bactericides properties extremely larger than those of any cleaning product commonly used. So the disinfection process is carried out efficiently, the device is equipped with various components to detect that your hands have been placed in the correct position and that are kept inside of it during the time required to complete the disinfection. In the case of detecting that the hands are not placed in the required position, or when one or both hands are removed from the device before concluding disinfection process, the device emits an alarm signal that warns about this situation and can send registered information used to restrict the entry of the user to sectors requiring the asepsis of hands to users who have failed to finish a proper disinfection, for example, blocking the doors, turnstiles, or by means of infrared light barriers that when passing produce alarm signals, among other possible forms.

It is therefore an object of the present invention to provide a device to eliminate germs and bacteria from the hands, especially designed to achieve the total asepsis of the hands of people working and/or should have access to certain sectors of the manufacturing industries and/or food fractionation, medicinal products, industry biological laboratories, chemical industries in general, operating rooms, etc. where it is required to maintain strict hygiene and asepsis conditions.

The cabinet contains a front opening for the entry of the hands to disinfect. The cabinet includes an outer box and an inner box in which is defined a cavity where the user must place their hands for the disinfection process. Between the rear, the side, the top, and the bottom walls of these boxes are spaces for the movement of the ozone gas into the cavity of the inner box where the user places their hands. The bottom, top, and side walls of the inner box include a plurality of slots for the passing and circulation of ozone between the inner box and the outer box during the disinfection process. The ozone generator is placed between the rear wall of the outer box and inside it. Adjacent to the ozone generator is arranged at least one fan to force the ozone to circulate inside the cabinet.

The ozone that tries to escape will be forced to go to the bottom of the barrier to be suctioned and forced to go through a system of Thermo-agitation in two steps with a Nichrome mesh, which will be at a temperature close to 60° C. From here, much of the ozone is destroyed thermally and continues with turbulent flow (stirring) until it reaches the second Nichrome mesh, which is close to the injection area (or upper zone) of the barrier.

The device includes a presence and hand position detector within the cabinet, a light indicator for the correct location of the hands, a sound indicator for the hands in the correct position, a timer/time counter of the process and interrupt time of the process by removal of one or both hands before default disinfection time, LEDs indicators for the elapsed time of the disinfection process, a light indicator disinfection time completed a luminous indicator of removal of one or both hands before the default time of disinfection, and an audible alarm of the removal of one or both hands before default disinfection time. (See FIGS. 1 and 2).

BRIEF DESCRIPTION OF DRAWINGS

For greater clarity and understanding of the present invention, it has illustrated in several figures that represent the preferred manner of preparation, all for example, where.

DETAILED DESCRIPTION OF THE INVENTION

Figure 1:
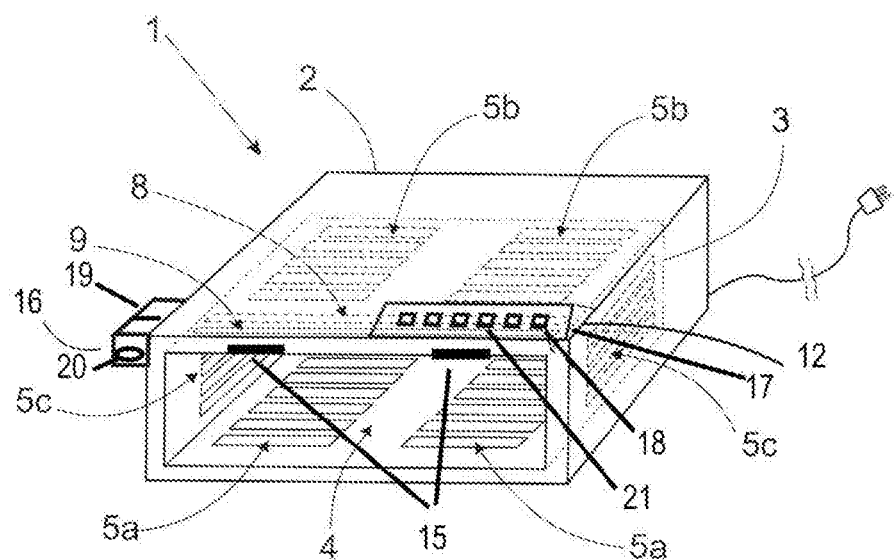
FIG. 1 is a perspective front view of the cabinet according to the present invention.
Figure 2:
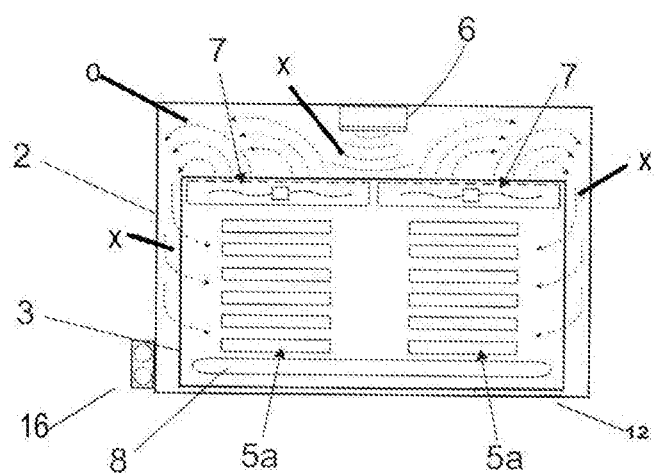
FIG. 2 is a top view of the cabinet, without the upper walls of the inner box and outer box, showing some of its main components.
Figure 3:
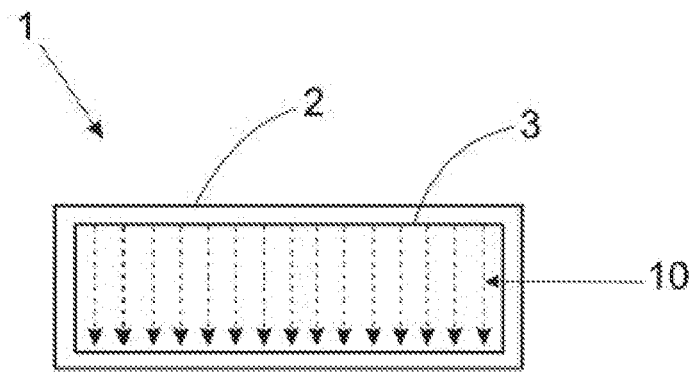
FIG. 3 is a front elevation view of the cabinet showing with descending arrows an air curtain to keep the cloud of ozone inside the cabinet during the disinfection process.
Figure 4:
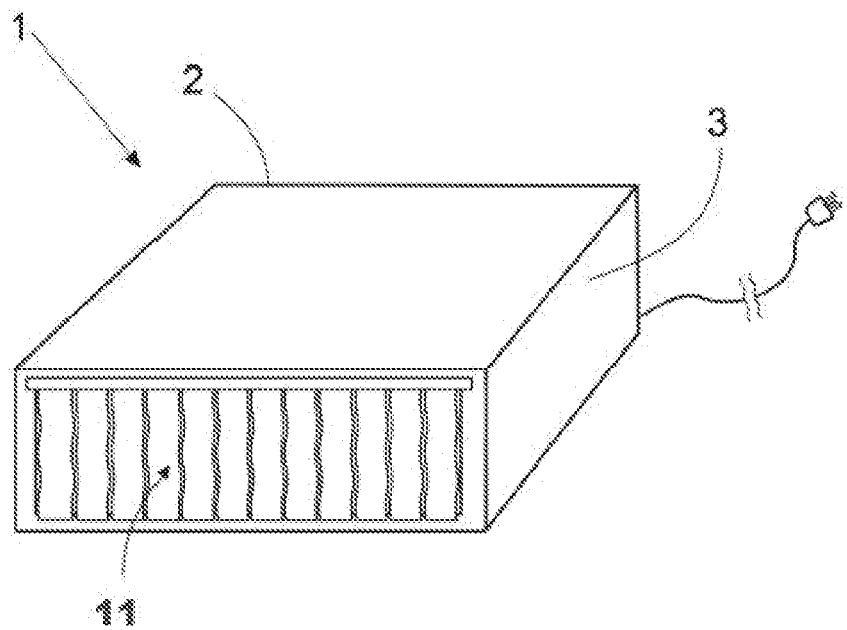
FIG. 4 is a perspective front view of the cabinet showing a plurality of hanging strips in the front opening of the cabinet that form a curtain containment of ozone within the cabinet and for obstruction of entry of impurities from the environment outside to the inside of the cabinet.
Figure 5:
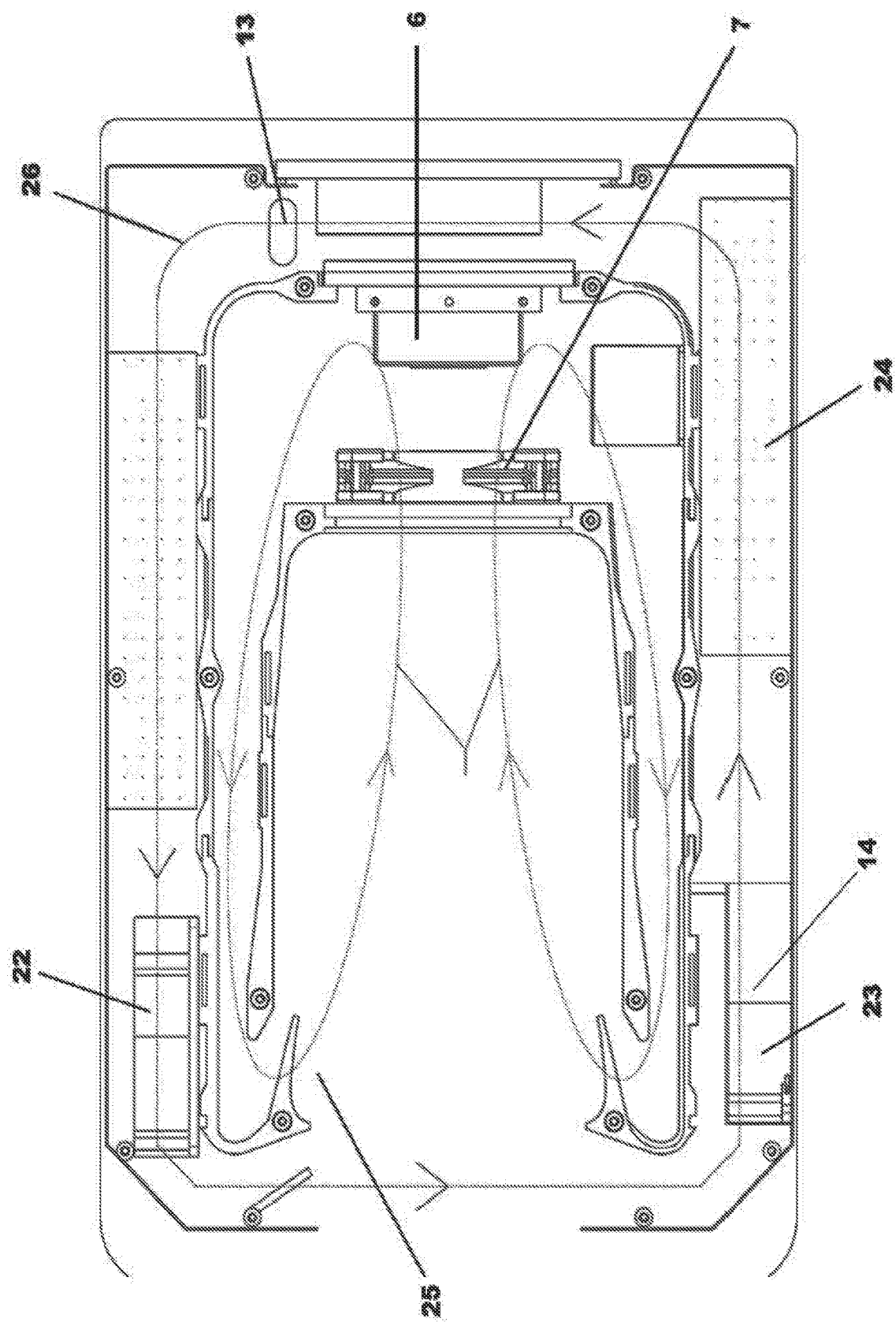
FIG. 5 is a perspective view of the cabinet showing the mesh of the Nichrome meshes of the two steps of the Thermo-agitation system.

FIGS. 1 to 3 shown a device 1 comprising a double box defined by an outer box 2 and an inner box 3 that includes a front opening 4 for the entry of the hands to disinfect. Between the posterior, lateral, upper, and bottom walls of the two boxes, there are respective spaces X for the movement of ozone gas O and/or air. The outer box 2 and the inner box 3 must be made of a material that does not react with ozone, for example, stainless steel 316L, PVDF (plastic), and PVC.

The bottom wall and the top wall of the inner box 3 have a plurality of slots 5a-5b, and their side walls include a plurality of slots 5c, which, as explained below, allow the passage and movement of ozone O during the disinfection process. Optionally, the front opening 4 can be covered by a plurality of hanging strips 11 as a curtain, whose purpose is to contribute to obstruct both the exit of ozone from the cabinet and the entrance of impurities from the outside environment.

The cut of FIG. 2 shows that between the rear wall of the outer box 2 and the inner box 3 there is located an ozone generator 6, e.g. ceramic, of sufficient power to generate a cloud of ozone in the quantity and the density required to achieve total asepsis of both hands of the user.

A couple of fans 7 laterally aligned among themselves are mounted on the back side of the inner box 3, and ahead of the ozone generator 6. The fans 7 forced the recirculation of the ozone on the space between the walls of the outer boxes 2 and the inner box 3, making it pass through the slots 5a, 5b and 5c of the walls of the inner box 3, so that it arrives in the enclosing form for both hands to be disinfected. The exact combination of ozone, and the speed with which it spreads, results in the time that the hands should be placed to be properly disinfected.

The forced circulation of air that distributes the ozone evenly, and in the required amount reaching simultaneously both hands placed properly, ensure the total disinfection.

In addition, there are placed two elements that ensure that the outside environment near the cabinet is free of ozone, or at least that a minimum amount is dispersed to avoid irritation of the respiratory tract of the person who completed the disinfection of their hands or who are in the vicinity of the cabinet.

The ozone O that tries to escape the cabinet will be forced to go to the bottom end of the barrier 10 to be sucked and forced to go through a two-step Thermo-agitation system. First, the ozone goes through a first thermal Nichrome mesh 13, which will be at a temperature close to the 60° C. A large amount of the ozone is thermally destroyed by the first thermal mesh 13. The ozone that is not destroyed continues with turbulent flow (stirring) until it reaches the second Nichrome mesh 14 (see FIG. 6), which is close to the injection zone (upper zone) of the barrier. The size and shape of the nichrome meshes will depend on the size and shape of the cabinet. The mesh may be made of any thickness.

The device 1 also includes a detector 15 for the presence and hand position within a cabinet, a light indicator 16 for the correct positioning of the hands, a sound indicator 17 for the correct position of the hands, a timer/time counter 12 for the processing and interruption by removal of one or both hands before default disinfection time. The timer/time counter 12 includes LEDs 18 to indicate the elapsed time of the disinfection process.

In addition, the device 1 includes a luminous indicator 19 of disinfection time completed, luminous indicator 20 for removal of one or both hands before default disinfection time, and an audible alarm 21 of removal of one or both hands before default disinfection time. (See FIGS. 1 and 2).

In the space X at the top end between the two boxes 2, 3, there are located fans 22 which help to move the residual ozone towards the barrier 10.

In the space X at the bottom between the two boxes 2, 3, there are located fans 23 which help suck ozone from the barrier 10.

Charcoal filters 24 may also be placed on the spaces x.

Figure 6:
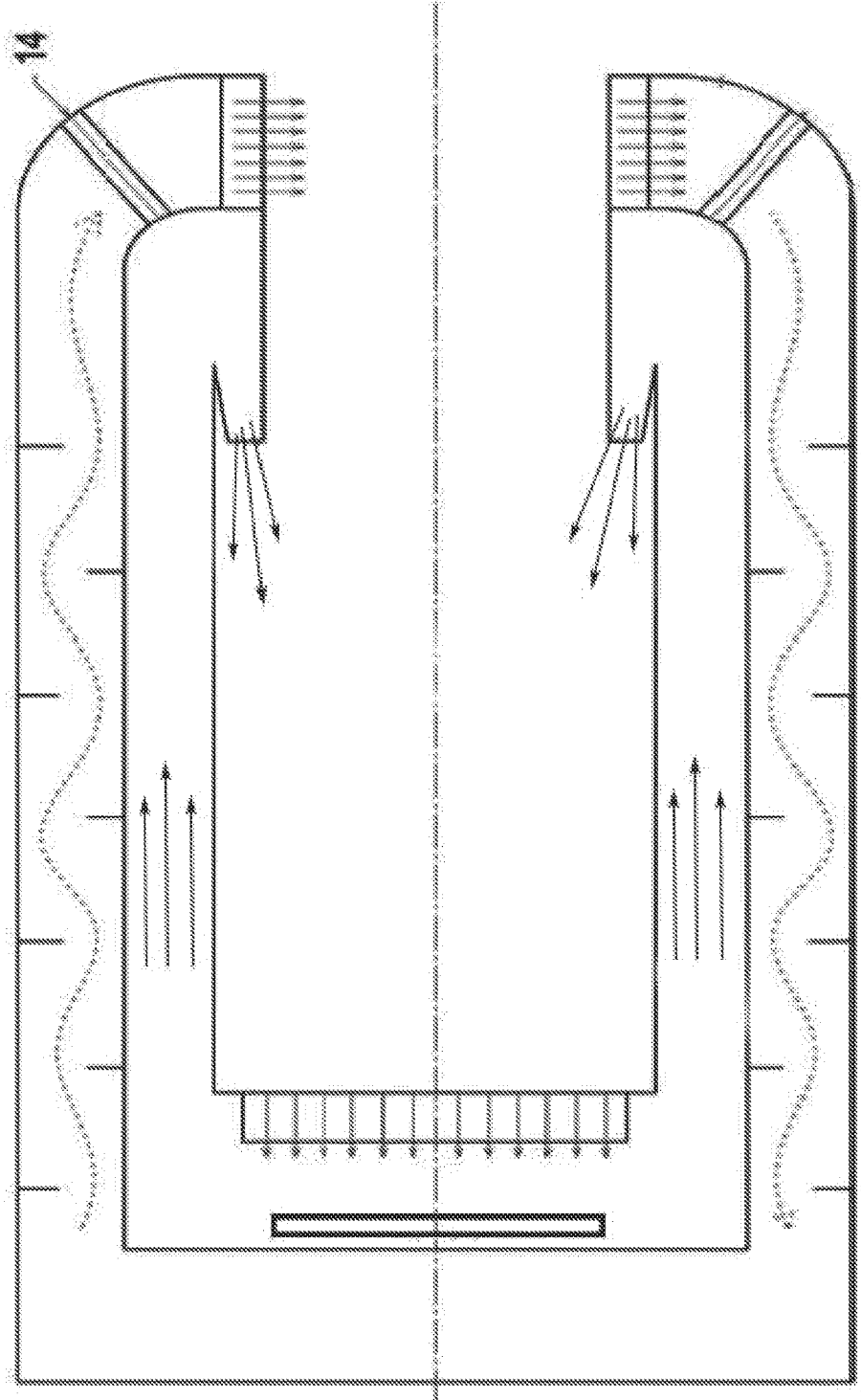
FIG. 6 is a top view of the cabinet showing the direction of the ozone movement and the ozone destroyer inside the cabinet.

FIG. 6 shows the cabinet including the ozone flow direction 25 and the ozone destroyer 26 flow direction of ozone inside the cabinet.

Another aspect of the invention of the ozone O is destroyed using the upper edge of the front side of the inner box 3 an ultraviolet lamp 8 by means of which, given the properties of the frequency of ultraviolet rays, destroy the residual ozone molecules scattered inside the cabinet and that try to exit the cabinet to the outside environment. A second additional element includes a curtain of air that forms a barrier that obstructs the exit of the ozone towards the environment.

As shown in FIG. 1, in the top front end of the inner box 3 and ahead of the UV light lamp 8, are located slots 9 through which passes the air, such as shown in FIG. 3, produces a barrier 10 that acts from the beginning of the disinfection process until a few moments after it is concluded.

When the user introduces its two hands inside of the cabinet 1, i.e. inside the inner box 3, the detector 15 of location and movements of the hands determines if they are in the correct position to start the process of total disinfection. Detection is performed using a technology of sensing based recognition of gestures and movements by mathematical algorithms. The detector 15 is commercially known as "Gesture Sensor", that allows to determine with a high degree of reliability if both hands have been introduced and are located correctly, if the hands are located on the right side, if both hands are positioned parallel to the floor of the cabinet and the required depth within the same, and detecting the opening of fingers among the required conditions to start the disinfection to be held with the necessary efficiency to achieve total asepsis. The detector 15 can be optical, capacitive, or other technology available today or in the future.

If the position of the hands is correct, a yellow light is turned on in the light indicator 16, and optionally, a sound indicator 17 of audio frequency emits a signal indicating to the user that it will be beginning the process of disinfection of the hands. From that moment, the ozone generator 6 is activated, the fans 7 begin to operate, the air barrier 10 is formed, and the timer 12 starts counting the time that the process will last, approximately 30 seconds, during which the user must leave the hands in the correct position to achieve a total asepsis. The user should place the palms of his hands down and separate the fingers.

By means of a visual indicator or 'display' of the LEDs 18, which defines a status bar graduated in proportion to the elapsed time of the disinfection process, the user sees how the time passes that he/her should keep their hands inside of the device to complete the disinfection.

Concluding the stipulated time and concluding the process, normally, the light indicator of time of disinfection 19 turns on a green light and a light indicator 20 generator of audio frequency emits a sound signal to indicated to the user to remove the hands from the cabinet 1 perfectly sanitized.

The gestures sensor activated a UV lamp 8, whose rays destroy the ozone molecules that could be on the device. The air barrier 10 stops when gestures sensor detects that the user withdrew his/her hands from the inside of the cabinet 1.

The time of the disinfection process and permanence of the hands of the user in the inside of the cabinet 1 is configurable in multiples of milliseconds, being necessary that the hands remain in the correct position for the pre-set time, so that the process is considered to be efficiently performed.

If the gestures sensor detects that the position of one or both hands is not correct, it actives an audible alarm 21 which emits a warning beep, or "beep" alarm, turns on a red light, and user must position the hands properly to start the disinfection of them again. In the event that one or both hands do not remain correctly positioned during the time preset for the disinfection process, the operation automatically stops the device until the hands are placed correctly.

From the moment in which the process is interrupted, is activated the timing of a predetermined time, called "resuming time", configurable in multiples of milliseconds. If during the resuming time, the user puts his/her hands in the correct position, the disinfection process is restarted once the gestures sensor detects the presence of both hands, correctly placed.

Once the resuming time is done, if detector 15 does not detect that the hands are correctly positioned inside the cabinet 1, the status bar stops, the process is completely cancelled, and the device returns to its initial state. The user is alerted of this situation through a visual indication or an alarm.

Another aspect of the invention, one device includes a light UV 8 lamp to destroy residual ozone.

Optionally, when deemed appropriate and sufficient, the device can also operate for one hand disinfection, which is configurable in the user's profile.

Having thus particularly described and given the nature of the present invention and form as it will be realized, pleads claim of ownership and exclusive right to:

What is claimed is:

1. A device to eliminate germs and bacteria from hands, the device comprising:
    a cabinet including a front opening for entry of the hands to be disinfected, the cabinet including:
    an outer box, the outer box having a front end, a rear end, a top end, a bottom end, a rear wall, side walls, a top wall, and a bottom wall;
    an inner box (3) placed inside the outer box (2), the inner box (3) having a cavity where the hands are placed, a front end, a rear end, a top end, a bottom end, a rear wall, side walls, a top wall, and a bottom wall;
    spaces between the rear, the side, the top and the bottom walls of the outer box and the inner box;
    a plurality of slots located in the top wall, bottom wall, and side wall of the inner box;
    an ozone generator located between the rear walls of the outer box and the inner box;
    fans located facing the ozone generator, the fans circulate the ozone through the cabinet, the ozone moves inside the cabinet by passing through the plurality of slots of the inner box;
    a first mesh made of nichrome located in the space between the rear walls of the outer box and the inner box, the first mesh is a heated mesh;
    a second mesh of nichrome located near the opening of the cabinet; and
    at least one aperture located in the front end near the top end of the inner box, the aperture allows the passing of air forming a curtain of air which forms an ozone barrier on the inside of the cabinet.

2. The device according to claim 1, wherein the front opening is covered by a plurality of hanging strips.

3. The device according to claim 1, further including a presence detector inside the cabinet.

4. The device according to claim 1, further including a light indicator for providing a signal for showing that the hands are placed correctly.

5. The device according to claim 1, further including a sound indicator for showing when the hands are in the correct position.

6. The device according to claim 1, further including a timer.

7. The device according to claim 6, wherein the timer includes a bar of LEDs to show elapsed time of the disinfection.

8. The device according to claim 1, further including a light indicator to show disinfection time completed.

9. The device according to claim 1, further including a luminous indicator to show if one or both hands are removed before a default disinfection time.

10. The device according to claim 1, further including an audible alarm to show if one or both hands are removed before a default disinfection time.

11. The device according to claim 1, further including a UV lamp located in the front end of the inner box.

12. A device to eliminate germs and bacteria from hands, the device comprising:
- a cabinet including a front opening for entry of the hands to be disinfected, the cabinet including:
- an outer box, the outer box having a front end, a rear end, a top end, a bottom end, a rear wall, side walls, a top wall, and a bottom wall;
- an inner box (3) placed inside the outer box (2), the inner box (3) having a cavity where the hands are placed, a front end, a rear end, a top end, a bottom end, a rear wall, side walls, a top wall, and a bottom wall;
- spaces between the rear, the side, the top and the bottom walls of the outer box and the inner box;
- a plurality of slots located in the top wall, bottom wall, and side wall of the inner box;
- an ozone generator located between the rear walls of the outer box and the inner box;
- fans located facing the ozone generator, the fans circulate the ozone through the cabinet, the ozone moves inside the cabinet by passing through the plurality of slots of the inner box;
- a first mesh is made of nichrome located in the space between the rear walls of the outer box and the inner box, the first mesh is a heated mesh;
- a second mesh of nichrome located near the opening of the cabinet;
- at least one charcoal filter located in the spaces between the rear, the side, the top and the bottom walls of the outer box and the inner box; and
- at least one aperture located in the front end near the top end of the inner box, the aperture allows the passing of air forming a curtain of air which forms an ozone barrier on the inside of the cabinet.

* * * * *